United States Patent [19]

Boessler et al.

[11] 4,112,215

[45] Sep. 5, 1978

[54] COPOLYMERIC RESIN BINDER POWDERS

[75] Inventors: Hanns Boessler, Darmstadt; Hubert Rauch, Weiterstadt, both of Germany

[73] Assignee: Rohm GmbH, Darmstadt, Germany

[21] Appl. No.: 769,290

[22] Filed: Feb. 16, 1977

Related U.S. Application Data

[62] Division of Ser. No. 603,608, Aug. 11, 1975, abandoned.

[30] Foreign Application Priority Data

Mar. 20, 1975 [DE] Fed. Rep. of Germany ....... 2512238

[51] Int. Cl.$^2$ ............................................. C08F 6/22
[52] U.S. Cl. .............................. 528/503; 260/29.6 H; 260/29.6 TA; 264/13; 424/33; 526/263; 526/264; 526/303; 526/312; 526/317; 526/320; 528/483; 528/499; 528/502
[58] Field of Search ................. 264/13; 528/483, 499, 528/502, 503

[56] References Cited

U.S. PATENT DOCUMENTS

| | | |
|---|---|---|
| 2,667,473 | 1/1954 | Morner et al. ...................... 260/85.7 |
| 3,365,409 | 1/1968 | Lanthier .............................. 260/29.6 |
| 3,753,958 | 8/1973 | Wingler et al. ................. 260/78.5 R |
| 3,787,340 | 1/1974 | Labana et al. ................... 260/23 XA |
| 3,803,111 | 4/1974 | Munro et al. .................... 260/89.5 S |
| 3,925,329 | 12/1975 | Heinrich et al. ................ 260/78.5 R |

Primary Examiner—Stanford M. Levin
Attorney, Agent, or Firm—Curtis, Morris & Safford

[57] ABSTRACT

Powders of physiologically-tolerable copolymers of vinyl and vinylidene monomers, said copolymers being useful as fast-dissolving resin binders for the preparation of pharmaceutical coatings, having a residual monomer content of less than 0.05 percent by weight, and having a primary particle size less than one micron; a method of preparing such powders by spray drying an aqueous dispersion of a copolymer under non-sintering temperature conditions; a method for preparing solutions for coating orally-ingestible dosage unit forms with said copolymers; and such dosage unit forms coated with said copolymers.

2 Claims, No Drawings

COPOLYMERIC RESIN BINDER POWDERS

This is a division of application Ser. No. 603,608, abandoned, filed Aug. 11, 1975.

The present invention relates to polymer powders adaptable to use as binders in the formulation of pharmaceutical coatings, to methods of making the same, to coated dosage unit forms, and to methods of making the latter.

Coatings on pharmaceutical dosage forms such as tablets, dragées, or pills, are predominantly prepared from solutions which contain a binder and, as a rule, pigments and fillers, in an organic solvent. These solutions contain undesirably high amounts of unreacted monomeric starting materials for the synthetic polymer. The residual monomers must subsequently be removed from the solution, a process which is difficult, laborious, and of only limited success. Thus, it has been sought to prepare synthetic polymers for coating purposes in a different way.

For example, the monomeric starting materials have been polymerized into a solid block in the absence of a solvent. This block is then ground and dissolved in a suitable organic solvent. However, the polymer powder obtained by grinding — just as does the solution polymer — contains undesirably large amounts of residual monomers. The fraction of these monomers can, to be sure, be reduced to about 0.2–0.4 percent by extraction and subsequent vacuum treatment. Nevertheless, this value is still undesirably high. Further, the solution of the polymer powder in organic solvents has proved to be an extremely time-consuming working method: solution times of 24 hours are common.

A commercial product produced by the precipitation of a resin binder from a liquid phase is already known in the art. Its content of residual monomers is between 0.15 and 0.3 percent. The rate of solution of this product is greater than that of a ground bulk polymer but still involves a period of hours. This product has also therefore not been found satisfactory.

The present invention has as an object the preparation of binder solutions for the preparation of pharmaceutical coatings, which solutions contain the smallest possible amount of residual monomer. A feature of the invention is the use of powders, in the preparation of film-forming coating solutions for dosage unit forms, which powders are obtained by spray drying an aqueous dispersion of a physiologically-tolerable vinyl copolymer soluble in organic solvents, said copolymer being insoluble in a portion of the pH region between pH 1.5 and 8 and being water-soluble or water-swellable in another portion of this region.

The preparation of a polymer solution by a process in which an aqueous dispersion of the polymer is first prepared, this dispersion is converted to a powder by spray drying, and the powder is then dissolved in an organic solvent is, to be sure, a roundabout method and would not be considered to involve technical progress if it were not accompanied by considerable additional advantages. Thus, the lowering of the residual monomer content achieved according to the process of the present invention is unexpectedly high: residual monomer contents below 0.05 percent are obtained. Further, it has been found that the polymer powder obtained by spray drying dissolves in an organic solvent in extremely short times, for example within 3 to 5 minutes. For this reason, the polymer powder is advantageously not dissolved in an organic solvent to give a coating solution by the manufacture of the powder, but is first so converted by the user. Thus, the powdered binder can be packed and stored in a considerably simpler manner than can a binder solution. Further, the powder has a smaller shipping weight and is not dangerously inflammable. The ultimate user can prepare a binder solution in whatever solvent he desires and in whatever concentration he desires. These are advantages which heretofore the consumer has only exercised reluctantly, since the available binder powders required solution times of several hours and even then gave no solution of a significantly reduced residual monomer content. The particular advantages of the powders used according to the present invention justify the relatively high technical effort involved in their preparation.

The spray drying process used for preparing the powder of the present invention is carried out most economically if the entrance temperature of the air used for drying is as high as possible. However, this is not the preferred embodiment of the present invention, since the polymer particles then strongly sinter together and no longer show the greatest possible solution rate. Rather, the spray drying process is advantageously carried out in such a manner that the polymer particles do not exceed the minimum film-forming temperature (MFT) of the polymer. The MFT is defined as the lowest temperature at which a thin layer of the aqueous dispersion of the polymer in question still forms a coherent film on drying.

Naturally, it is suitable to proceed from the outset with a polymer dispersion having a low residual monomer content. Methods for carrying out an emulsion polymerization to obtain a low residual monomer content are known. As the most important, a post-reaction time of several hours subsequent to the exothermic phase of the polymerization should be mentioned. However, on coagulating such a dispersion, a residual monomer content which cannot be lowered below 0.15 percent to 0.3 percent is obtained. The spray drying process, thus, offers a double advantage: on the one hand, the residual monomer content is reduced in a very effective manner and, on the other hand, a powder of extraordinary fineness and high solution rate is obtained.

The powders preferred for use in the present invention, in whose preparation the MFT is not exceeded, can be recognized in that the individual powder grains comprise loosely aggregated fine particles, hereinafter referred to as primary particles. This condition can be recognized under a microscope, particularly at about 40 × magnification under a reflecting stereomicroscope. The grains can be disintegrated with a needle practically without mechanical resistance, like a loose snowball, leaving crumbled soft fragments adhering to the disintegrating tool. In contrast, if the MFT is exceeded during spray drying the fine (primary) particles of the dispersion flow together until each separate powder grain forms a completely glazed mass. Whereas a microphotograph of the aforementioned unglazed products is suggestive of snow, the glazed particles have the appearance of ice. They are hard and brittle and can only be broken up by overcoming their mechanical resistance. The solubility time of such a powder is a multiple of that of the preferred form.

The aim of using the binders as coating agents for pharmaceutical dosage forms, the method of their preparation from an aqueous dispersion, and, finally, the method of which the binders are used all make certain solubility properties of the binding agents necessary. The binders must be soluble in organic solvents which are customarily used for medicament coating lacquers. In order to be able to form an aqueous dispersion, the binders must be water-insoluble in at least a portion of the pH region between pH 1.5 and 8. In another portion of this region, however, they must permit release of the active medicinal agent from the coated dosage unit form, i.e. in this pH region they must be either water-soluble or at least so readily swellable by water that the release of the active agent by diffusion is made possible.

These solubility properties are achieved by balancing in the copolymer, by a method known per se, those monomer components respectively having hydrophilic and hydrophobic properties which are employed in synthesizing the binders. Hydrophobic monomer components promote solubility in organic solvents and limit solubility in water. Hydrophilic monomer components promote swellability or solubility in water and, depending on whether they are neutral or contain acid or basic groups, influence accordingly the dependence of these solubility properties on the pH value. The invention permits the preparation of all known binders for pharmaceutical coatings in a powder form, with the advantages described above, providing the binders have the necessary solubility properties.

Neutral binders give pharmaceutical coatings which become diffusion-transparent independently of the pH value of the surrounding medium. For example, they may comprise a principal portion of monomers containing hydroxy groups, such as hyroxyalkyl ester of $\alpha,\beta$-unsaturated mono- or di-carboxylic acids. At a content of hydroxy groups of 1 to 12 weight percent, which corresponds to a content of monomers having hydroxy groups between about 10 percent and 80 weight percent, these binders are insoluble in water, independently of the pH values, but are swellable. Therefore, they can be prepared in the form of a dispersion. Like the monomers containing hydroxy groups, vinyl pyrrolidone, acrylamide, or methacrylamide, as well as monomers having quaternary ammonium groups, promote hydrophilicity independently of the pH value. Therefore, these monomers may be present in the vinyl copolymers according to the invention always only in such amounts that the copolymers are not yet water-soluble.

Pharmaceutical coatings containing basic groups are only soluble or diffusion-transparent in the stomach juices: those having acid groups are soluble or diffusion-transparent only in the intestinal juices. Coating agents of this type in the form of dispersions are known from German Pat. No. 2,135,073. Although they are provided for the direct coating of pharmaceutical dosage forms, they can be converted into a powder by spray drying, which powder can then be used according to the present invention. They contain vinyl copolymers which comprise from 10–50 percent by weight of monomers having a carboxy group and/or a monoalkyl- or dialkyl-aminoalkyl ester group. If they contain carboxy groups, they are insoluble in water at pH values below 7 and can be prepared in this pH region as dispersions. Dosage unit forms covered with this binder are insoluble in the acid milieu of the stomach and are first converted to a soluble or swollen condition in the neutral or weakly alkaline milieu of the intestinal juices. In contrast, binders having a content of monoalkyl- or dialkyl-aminoalkyl ester groups are soluble or swellable in acid milieu so that they can be prepared in the form of a dispersion in the alkaline region. Similar coating forms are known from German Pat. Nos. 1,090,381 and 1,219,175. The latter contain dialkyl aminoalkyl amides of unsaturated acids.

The binders for use according to the invention are accordingly preferably those vinyl copolymers formed from mono-ethylenically unsaturated, free radical-polymerizable compounds of which from 5–80 percent by weight are soluble in water. The water-soluble monomers are preferably ethylenically $\alpha,\beta$-unsaturated polymerizable mono- or di-carboxylic acids, their amides, their hydroxyalkyl esters, their monoalkyl amino- and dialkyl amino-esters, water-soluble quaternization products of the aforementioned compounds containing amino groups, vinyl pyrrolidone or N-vinyl imidazole. Among these, acrylic acid, methacrylic acid, and the aforementioned derivatives of these acids are particularly preferred.

In addition to these monomers, those monomers which if polymerized alone would form water-insoluble homopolymers form from 20–95 percent by weight of the vinyl copolymer. Preferred monomers of this type are styrene, vinyl acetate, and, preferably, alkyl esters of acrylic acid or methacrylic acid having from 1–10 carbon atoms in the alkyl portion. The amount of the last-mentioned monomers, which are difficultly soluble or insoluble in water, present in the vinyl copolymer depends on the degree of hydrophilicity of the water-soluble monomers copolymerized therewith. If very strongly hydrophilic monomers, such as polymerizable quaternary ammonium compounds, are employed, a considerable fraction of hydrophobic monomers will be necessary in order to assure the water-insolubility of the copolymer. Conversely, less hydrophilic monomers, such as the hydroxyalkyl esters of acrylic acid or methacrylic acid, may predominate over the hydrophobic monomers.

The dispersions to be employed for the preparation of the binder powder are prepared according to known methods to have a polymer content of, for example, 20–50 percent. In choosing an emulsifying agent, the ability of the monomers or of the polymer to form salts must be taken into account. Thus, monomers containing carboxy groups are preferably polymerized in the presence of anionic emulsifiers, while monomers containing amino ester groups are preferably polymerized in the presence of cationic emulsifiers. Non-ionic emulsifiers, for example the oxyethylated fatty alcohols, fatty acid amides, or alkylphenols having about 20–100 mols of ethylene oxide units per mol of the hydrophobic basic compound, are suitably used with both monomer groups and can be employed for the polymerization of monomers containing amino groups also in combination with anionic emulsifiers. Exemplary of the anionic emulsifiers are soaps or the compounds obtained from the aforementioned ethylene oxy-adducts by sulfating and neutralizing. For monomer mixtures containing a large number of carboxy groups, mixtures of non-ionic and anionic emulsifiers are advantageously employed. For the polymerization of monomer mixtures containing amino groups, suitable cationic emulsifiers are, for example, (di-isobutylphenoxy-ethoxyethyl)-dimethyl-benzyl-ammonium-chloride or stearyl-dimethyl-benzyl ammonium chloride. They may optionally be employed in admixture with non-ionic emulsifiers. The amount of emulsifier employed is at least 0.5 percent by weight, and preferably from 1–5 percent by weight of the aqueous phase. The preferred methods of preparing the dispersions are the emulsion-addition method and the monomer-addition method. In these, the monomer mixture per se, or in the form of an aqueous emulsion, is gradually introduced into the polymerization vessel. As a rule, polymerization is carried out at 60° C.–90° C. and potassium- or ammonium-persulfate or 4,4'-dicyano-4,4'-azo-valerianic acid is used as the initiator. The molecular weight can be controlled by a choice of the amount of initiator or by the addition of sulfur-containing regulating agents, such as thioglycolic acid-2-ethylhexyl ester.

The aqueous binder dispersion obtained is dehydrated in a spray drying apparatus which can be equipped with a spray plate or spray nozzle. The temperature of the air blown into the spray tower for drying is chosen to be only so high, in the preparation of the preferred products, that the primary particles in the dispersion, which have a size below 1 micron, do not sinter or fuse together in the individual droplets. As long as the material to be dried still contains a lot of water, the air temperature can be considerably above the particle temperature. Since it is extraordinarily difficult to measure the particle temperature itself, the question whether the particle temperature during the dehydration process has been continuously below the permissible maximum temperature can be most surely and easily answered by inspecting the dried particles under a microscope. If the particles are glazed, it can be concluded that they have reached too high a temperature, perhaps for only a short period of time, and that therefore the ambient temperature was also too high. For the majority of the polymer compositions in question, glazing occurs in a temperature region from 80° C.–120° C. Thus, copolymers having an MFT greater than 80° C. are preferred for use according to the invention. If dehydration has proceeded to a water content of 10 percent or less, the air temperature should not lie above, or only a little above, the temperature at which the particles glaze. At the end of the drying process, the air temperature must be below 100° C. A temperature of 60° C.–70° C. is to be preferred. By a suitable choice of the entrance temperature of the air and the ratio of the amounts of air to dispersion, the spray drying process can be carried out in such a manner that the air temperature falls below the glazing temperature as a result of heat consumption on evaporation of water as dehydration increases. In particular cases it is easy to determine by microscopic inspection whether the drying conditions employed are suitable for the production of products having the preferred, most finely-divided, condition.

The powdered binders obtained must be protected from moisture until they are dissolved. For the preparation of coating solutions for pharmaceutical dosage units, the powdered binder, in the desired amount, is stirred into a suitable organic solvent and goes into a clear solution within a few minutes. Useful binder concentrations are between 5 percent and 25 percent. As the solvents, lower alcohols and ketones or mixtures thereof are generally used, for example ethanol, propanol, isopropyl alcohol, acetone, and the like. The binder solutions obtained in this manner have all the properties of the known solutions now commercially available and can be pigmented and worked up in the same manner.

A better understanding of the present invention and its many advantages will be had by referring to the following specific Examples, given by way of illustration.

EXAMPLE 1

Preparation of the Dispersion 1.4 g of ammonium peroxy disulfate and 3.5 g of a $C_{15}$-paraffin sulfonate (commercially available as "Emulsifier K30", Bayer AG) are dissolved in 1394 g of water at 80° C. in a 2 liter vessel. A monomer mixture prepared from 300 g of methylmethacrylate 300 g of methacrylic acid, and 3.0 g of thioglycolic acid-2-ethylhexylester is added dropwise at 80° C. to the solution with stirring over a period of four hours. Subsequently, the batch is maintained for 2 hours at 80° C., cooled, and filtered through a fine-mesh steel sieve. The dispersion has a solids content of 30 percent, a particle size of about 0.1 micron, and a MFT > 90° C.

Drying of the Dispersion (A) The dispersion is introduced into a spray drying apparatus equipped with a so-called dual nozzle in co-current with air at 150° C. The ratio of dispersion to air is so adjusted that the sprayed material leaves the apparatus at an air exit temperature of 65° C. in the form of a dry, finely-divided, white-to-transparent powder which contains no glazed portions.

(B) The procedure under (A) above is followed with the difference that the spray drying apparatus is equipped with a rapidly-rotating atomizer disc (45,000 rpm). Hot air at a temperature of 240° C. is introduced in countercurrent centrally directly under the atomizing disc.

(C) Comparison Example without Spray Drying

The dispersion is poured into a drying tray lined with a synthetic resin film in a layer 1 cm thick and is then dried overnight at 50° C. in an air-circulating drying cabinet. The dried material, present in fragments, is subsequently pulverized in a mill.

(D) Comparison Example Employing a Ground Bulk Polymer

A monomer mixture containing 1.0 kg of methylmethacrylate, 1.0 kg of methacrylic acid, 1 g of azo-diisobutyric acid dinitrile, and 5 g of $\beta$-mercaptoethanol is added to a film bag and polymerized in a water bath. Subsequently, the material is heated for 8 hours at 115° C. The bulk copolymer obtained is sub-divided in a mill, washed twice with 4-fold portions of 5 percent isopropyl alcohol at 70° C., and dried in a fluidized bed granulator.

EXAMPLE 2

Preparation of the Dispersion 0.7 g of ammonium peroxydisulfate, 10.5 g of the sodium salt of an adduct prepared from tri-isobutylphenol and 7 mols of ethylene oxide (50 percent, commercially available as "Hostapal BV", Hoechst AG), and 10.5 g of an adduct prepared from iso-nonylphenol and 9 mols of ethylene oxide are dissolved in 700 g of distilled water at 80° C. in a vessel. A monomer mixture comprising 210 g of methylmethacrylate, 90 g of methacrylic acid, and 1.5 g of thioglycolic acid-2-ethylhexylester is added dropwise to the solution at 80° C. with stirring over a period of 4 hours. After the end of the addition, the batch is held for an additional 2 hours at 80° C., is cooled to room temperature, and filtered through a fine-meshed steel sieve. A low-viscosity dispersion containing 31 percent of solids is obtained. The average particle size is about 0.1 micron and the MFT is > 90° C.

Drying of the Dispersion (E) Drying is carried out as in Example 1(B) with the difference that the hot air is introduced at 120° C. The exit temperature of the air is 65° C.

(F) Comparison Example without Spray Drying

The procedure in Example 1(C) was followed.

(G) Comparison Example Involving Preparation of a Ground Bulk Polymer.

A monomer mixture comprising 1.4 kg of methylmethacrylate, 0.6 kg of methacrylic acid, 1 g of azodiisobutyric acid dinitrile, and 5 g of β-mercaptoethanol is introduced into a film bag and polymerized in a water bath. Subsequently, the batch is heated for 8 hours at 115° C. The bulk polymer obtained is ground in a mill, washed twice with four-fold portions of 5 percent of isopropyl alcohol at 70° C., and dried in a fluidized bed granulator.

Preparation of Binder Solutions from Products (A) – (G)

In each case, 16 g of the powdered products (A) – (G) are shaken at room temperature in 100 g of the solvent indicated. The solution times are given in the Table.

TABLE

| Product | Residual Monomer Content | Solvent | Solution Time |
| --- | --- | --- | --- |
| A | <0.015% | Isopropanol/acetone, 6:4 | 3 minutes |
| | | Isopropanol/H$_2$O, 97:3 | 5 minutes |
| B | <0.015% | Isopropanol/acetone, 6:4 | 90 minutes |
| C (Comparison) | 0.15% | Isopropanol/acetone, 6:4 | 3 hours, 15 minutes |
| | | Isopropanol | >24 hours |
| D (Comparison) | 0.3% | Isopropanol/acetone, 6:4 | 6 hours |
| | | Isopropanol | 8 hours |
| E | <0.015% | Isopropanol/acetone, 6:4 | 3 minutes |
| | | Isopropanol/H$_2$0, 97:3 | 2 minutes |
| | | Isopropanol | 15 minutes |
| F (Comparison) | 0.15% | Isopropanol/acetone 6:4 | 1 hour |
| | | Isopropanol | ca. 12 hours |
| | | Isopropanol/H$_2$O, 97:3 | ca. 12 hours |
| G (Comparison) | 0.3% | Isopropanol/acetone, 6:4 | 6 hours |
| | | Isopropanol | 40 hours |

EXAMPLE 3

12 g of 30 percent aqueous hydrogen peroxide and 7.5 g of cocoamine hydrochloride are dissolved in 560 g of water. 40 g of methacryloyloxyethyl-trimethylammonium chloride are added and the mixture is heated to 90° C. 144 g of isobutyl methacrylate are added within 10 minutes. After a 10 minutes brake, 260 g of isobutyl methacrylate are added dropwise within a 2 hours period. The temperature of 90° C is kept for another 2 hours. Then, the latex is cooled to room temperature and passed through a fine-mesh steel sieve. The solids content amounts to 40 percent by weight. The particle size is about 0.1 micron; the MFT is more than 90° C, and a residual monomer content amounts to 0.37%, based on the dry weight of the resin. By spray drying as in Example 1 B, the resin is obtained as a fine white powder with a residual monomer content of less than 0.01% b.w.

EXAMPLE 4

0.4 g of ammonium peroxy disulfate, 0.4 g of sodium paraffin (C$_{15}$) sulfonate, and 80 g of itaconic acid are dissolved in 775 g of water at 80° C. 120 g of methyl methacrylate are added dropwise within the next 4 hours with stirring. Simultaneously, a solution of 1.84 g of the emulgator mentioned above and 2.4 g ammonium peroxy disulfate is dropped into the mixture from a second dropping funnel. The temperature is kept for another 4 hours at 80° C. Then, water vapour is passed through the latex for about 20 minutes under slight vacuum such that the dispersion is kept boiling at 80° C. The resulting 20 percent resin dispersion has an average particle size of about 0.1 micron, a MFT of more than 90° C and a residual monomer content of 0.12%. The latex is spray dried as in Example 1 B and thus converted to a fine powder with a residual monomer content of 0.042% b.w. It is readily soluble in a isopropanol-acetone-mixture (1:1).

EXAMPLE 5

The proceeding of Example 4 is repeated with the difference that styrene is used instead of methyl methacrylate. A 19% aqueous resin dispersion is obtained having an average particle size of about 0.1 micron and a MFT of more than 90° C. By spray drying as in Example 1 B, a powder is obtained having a residual monomer content of 0.04% b.w. It is readily soluble in dioxane.

EXAMPLE 6

2.4 g ammonium peroxy disulfate and 16 g of an emulsifier are dissolved in 800 g of water at 80° in a 2 l reaction vessel. The said emulsifier is a reaction product of 1 mole of triisobutyl phenol and 7 moles of ethylene oxide which is sulfated and neutralized with sodium hydroxyde. A mixture of 180 g of methyl methacrylate and 20 g of 1-vinyl imidazole is added dropwise to the solution within the next 4 hours. The polymerisation proceeds at 80° C which temperature is kept constant for another 4 hours after completition of the monomer addition. Then, water vapour is passed through the latex for 20 minutes under slight vacuum. The resulting latex has a solids content of 16% b.w., an average particle size of about 0.1 micron and a MFT of more than 90° C. The residual monomer content of 0.19% b.w. (based on the dry weight) is lowered during the spray drying process to 0.05% b.w. The resulting powder is readily soluble in an isopropanol-acetone-mixture (1:1).

EXAMPLE 7

0.35 g of ammonium peroxy disulfate and 0.21 g of sodium dodecyl sulfate are dissolved in 300 g of water at 80° C. A preformed emulsion of 270 g of methyl methacrylate, 30 g of methacrylamide, 1.55 g of sodium dodecyl sulfonate, and 1.05 g of ammonium peroxy disulfate in 400 g of water is added dropwise at 80° C.

The resulting latex is kept at 80° C for another 4 hours, then water vapour is introduced for a 20 minutes period under slightly reduced pressure. A 30 percent latex is formed having a residual monomer content of 0.09% b.w. (on a dry weight basis). The average particle size is about 0.1 microns, the MFT is more than 90° C. The latex is spray dried as in Example 1 B, providing a fine powder with a residual monomer content of 0.04% b.w. which is readily soluble in an isopropanol-acetone-mixture (1:1).

EXAMPLE 8

An emulsion is prepared from 125 g of methyl methacrylate, 125 ethylene glycol monomethacrylate, 13 g of a reaction product of 1 mole of isononyl phenol and 100 moles of ethylene oxide as an emulsifying agent, 0.18 g of ammonium peroxy disulfate, 0.25 g sodium pyrosulfite, 3.75 mg of Fe(II) sulfate and 450 g of water. Polymerisation proceeds with permanent stirring of the emulsion. After completition of the polymerisation reaction the resulting latex is cooled to 30° C and 13 g of the emulsifying agent mentioned above, 125 g of methyl methacrylate and 125 g of ethylene glycol monomethacrylate are added and emulsified by stirring. The polymerisation reaction is continued by the addition of 0.18 ammonium peroxy disulfate and 0.25 g of sodium pyrosulfite. After cooling, the latex is passed through a fine-mesh steel sieve. The resulting latex of 51% b.w. of resin content has an average particle size of 0.1 micron and a MFT of more than 90° C. The residual monomer content is 0.04% b.w. of the dry weight. The latex is spray dried as in Example 1 B and yields a fine powder with a residual monomer content of 0.01% b.w. It is readily soluble in dioxane.

EXAMPLE 9

0.5 g of 4,4'-azobis-(4-cyano valeric acid sodium salt) and 1 g of polyoxyethylene sorbitan monostearate are dissolved in 400 g of water at 80° C. An emulsion prepared from 800 g of methyl methacrylate, 200 g of dimethylamino ethyl methacrylate, 5 g of 2-ethyl-hexyl thioglycolate, 2.4 g of sodium cetyl stearyl sulfate, 24 g of polyoxyethylene sorbitan monostearate, 1.5 g 4,4'-azobis-(4-cyano valeric acid sodium salt) and 600 g of water is added dropwise to the said solution within 4 hours at 80° C. This temperatur is kept constant for another 4 hours. Then, the latex is cooled to room temperature and passed through a fine-mesh steel sieve. A 49% latex is obtained, the residual monomer content of which is lowered by spray drying from 0.24% b.w. to less than 0.05% b.w. The resulting powder is soluble in a mixture of acetone, isopropanol, and water (16:16:1).

EXAMPLE 10

An emulsion prepared from 280 g vinyl acetate, 120 g of methacrylic acid, 2 g of 2-ethyl-hexyl thioglycolate, 14.4 g of the emulsifying agent used in Example 6, and 14.4 g of a reaction product of 1 mole isononyl phenol, and 8.5 to 9 moles of ethylene oxide and 970 g of water is added slowly within a 4 hours period at 80° C to a solution of 0.32 ammonium peroxy disulfate and 1.6 g of each of the two emulsifying agents mentioned above in 640 g of water. The mixture is kept at 80° C for another 4 hours, cooled to room temperature and filtered through a fine-mesh steel sieve. The resulting latex has a solids content of about 10% b.w. Spray drying of the latex yields a fine powder with a residual monomer content of less than 0.05% b.w. It is readily soluble in an isopropanol-acetone-water-mixture (16:16:1).

EXAMPLE 11

An emulsion prepared from 450 g of methyl methacrylate, 150 g of vinyl pyrrolidone, 20 g of a reaction product of 1 mole isononyl phenol and 100 moles of ethylene oxide, 2.1 g of 4,4'-azobis-(4-cyano valerianic acid sodium salt) and 840 g of water is added slowly within 4 hours at 80° C to a solution of 0.7 g of the catalyst mentioned above and 6 g of the emulsifying agent mentioned above. After 2 hours at 80° C, the latex is cooled to room temperature and filtered through a fine-mesh sieve. The resulting latex has a solids content of 30% b.w., a MFT of more than 90° C and an average particle size of 0.1 micron. By spray drying of the latex in the manner described in Example 1 B a fine powdery product is obtained having a residual monomer content of 0.01% b.w. It is readily soluble in a mixture of isopropanol, acetone, and water (16:16:1).

What is claimed is:

1. The method of making a copolymer powder having a residual monomer content therein of less than 0.05 percent by weight and having a primary particle size less than one micron in diameter, said powder being adaptable to rapid solution in an organic solvent to form a solution for coating a core comprising a therapeutically active ingredient, which method comprises spray drying an aqueous dispersion of copolymer particles at a temperature such that the temperature of the copolymer particles does not exceed the minimum film-forming temperature of the copolymer, said dispersion being prepared by the aqueous emulsion polymerization of monomers to give particles of a size less than one micron in diameter of a physiologically tolerable copolymer comprising (a) 5 to 80 percent by weight of a water-soluble monomer selected from the group consisting of $\alpha,\beta$-unsaturated mono- and dicarboxylic acids, acrylamide, methacrylamide, hydroxy lower alkyl esters of acrylic acid and methacrylic acid, monoalkyl- and dialkyl-amino lower alkyl esters of acrylic acid and methacrylic acid, quaternary ammonium salts of such amino lower alkyl acrylates and methacrylates, vinyl pyrrolidone, and vinyl imidazole; and
   (b) 95 to 20 percent by weight of a monomer selected from the group consisting of styrene, vinyl acetate, and alkyl esters of acrylic acid and methacrylic acid having 1 to 10 carbon atoms in the alkyl portion thereof;
   the relative amounts of monomers (a) and (b) in said copolymer being such that the minimum film-forming temperature thereof is greater than 80° C., said copolymer further being water-insoluble in one portion of the region between pH 1.5 and pH 8 and water-soluble or water-swellable in another portion of said region.

2. A method as in claim 1 wherein said copolymer comprises, as monomer component (a), a member selected from the group consisting of acrylic acid, methacrylic acid, acrylamide, methacrylamide, hydroxy lower alkyl acrylates and methacrylates, monoalkyl- and dialkyl-amino lower acrylates and methacrylates, and quaternary ammonium salts of such amino lower alkyl acrylates and methacrylates.

* * * * *